United States Patent [19]
Rohde

[11] Patent Number: 5,876,351
[45] Date of Patent: Mar. 2, 1999

[54] PORTABLE MODULAR DIAGNOSTIC MEDICAL DEVICE

[75] Inventor: Mitchell M. Rohde, Ann Arbor, Mich.

[73] Assignee: Mitchell Rohde, Ann Arbor, Mich.

[21] Appl. No.: 831,607

[22] Filed: Apr. 10, 1997

[51] Int. Cl.⁶ .................................................. A61B 5/0404
[52] U.S. Cl. ........................... 600/523; 600/522; 600/509
[58] Field of Search ..................................... 600/509, 513, 600/520, 522, 523

[56] References Cited

U.S. PATENT DOCUMENTS

| | | | |
|---|---|---|---|
| 4,082,084 | 4/1978 | Lipscher ................................... | 600/513 |
| 4,715,385 | 12/1987 | Cudahy et al. .......................... | 600/523 |
| 4,751,931 | 6/1988 | Briller et al. ............................ | 600/513 |
| 5,095,798 | 3/1992 | Okada et al. . | |
| 5,184,830 | 2/1993 | Okada et al. . | |
| 5,307,263 | 4/1994 | Brown ..................................... | 600/509 |
| 5,678,562 | 10/1997 | Sellers ..................................... | 600/509 |
| 5,678,571 | 10/1997 | Brown ..................................... | 128/905 |
| 5,687,734 | 11/1997 | Dempsey et al. ....................... | 600/509 |

OTHER PUBLICATIONS

"AMP New Age Holter Recorder", http://www.sana–med.com/ampecg.html, Sana–Med, Inc., pp. 1–3, (Jul. 20, 1998).

"Calculating Checksums", http://www.bpwl.com/ar/features/damaged/consoles/gbsum.htm, 2 Pages, (Jul. 29, 1998).

"Cardiax", http://www.medisoft.hu/cardiax/, International Medical Equipment Developing Co. Ltd., 4 Pages, (Jul. 29, 1998).

"ECG Package for PCs", wysiwyg://30/http://www.byte.com/art/9603/sec19/art9.htm, MRT International, 2 Pages, (Jul. 29, 1998).

"Gameboy Cartridges", *Ninetendo,* http://fly.hiwaay.net/~jfrohwei/gameboy/gb.html, 2 Pages, (Jul. 30, 1998).

"Gameboy Internals (CPU); Gameboy Internals (LCD section); Gameboy Internals (Power and Ex. ROM)", http://fly.hiwaay.net/, jfrohwei/gameboy/gameboy1.gif, Schematics for Gameboy Computer Program, (3 Pages).

"MAC PC Resting ECG Analysis System: Features", http://www.mei.com/products/macpc.features, Marquette Medical Systems, 1 page, (Jul. 29, 1998).

"MAC PC Resting ECG Analysis System: Specifications", http://www.mei.com/products/macpc.specs.html, Marquette Medical Systems, 3 Pages, (Jul. 30, 1998).

"Miniature ECG Telemetry System CG–100 (Arrhythmia Monitoring with Computerized Event Detection)", http://www.cardguard.com/prod6.html, Card Guard Scientific Survival Ltd., 3 Pages, (Jul. 30, 1998).

"PC–ECG (Medcare Systems Pty Ltd)", Http://www.bsl.unsw.edu.au/new/pcecg/pcecg.htm, At the Heart of Innovation, 1 Page, (Jul. 30, 1998).

"PC–ECG 1200", http://www.netvision.net.il/~norav/, norav/, Norav Medical Ltd., 1 Page, (Jul. 30, 1998).

"PC–ECG Overview", http://www.bsl.unsw.edu.au/new/pceg/overview.htm, Biomedical Systems Laboratory, 2 Pages, (Jul. 30, 1998).

"QRS–Card", http://grscard.com/products.htm, Pulse Boimedical, Inc., 2 Pages, (Jul. 30, 1998).

"Resting ECG", http://www.mortara.com//newages/resting-.htm, Marquette Medical Services, 2 Pages, (Jul. 30, 1998).

(List continued on next page.)

*Primary Examiner*—William E. Kamm
*Assistant Examiner*—George R. Evanisko
*Attorney, Agent, or Firm*—Schwegman, Lundberg, Woessner & Kluth, P.A.

[57] ABSTRACT

A portable modular diagnostic medical device. The medical device is based on a portable multipurpose computerized platform, such as those designed primarily for playing video games. A medical component such as a cartridge is removably connected to the platform, and has specialized circuitry specific to a predetermined diagnostic medical function, such as the monitoring of electrocardiograms (ECGs). Different medical functionality is provided for by removably connecting different components into the portable multipurpose computerized platform.

4 Claims, 11 Drawing Sheets

OTHER PUBLICATIONS

"SEER XT Ambulatory Digital Analysis Recorder: General Information", http://www.mei.com/products/seerxt.info.html, Marquette Medical Systems, 1 Page, (Jul. 30, 1998).

"SEER XT Ambulatory Digital Analysis Recorder: Specifications", http://www.mei.com/products/seerxt.specs.html, Marquette Medical Services, 2 Pages, (Jul. 30, 1998).

"Summary of Performance Requirements for Electrocardiographs", *Biopotential Amplifiers,* Webster, pp. 298–300, (1992).

"Technical", http://www.bpwl.com/ar/features/damages/consoles/gb–tech.htm, Damaged Cybernetics, 1 Page, (Jul. 30, 1998).

"Technical Specifications", http://www.bsl.edu.au/new/pcecg/specs.htm, Biomedical Systems Laboratory, 2 Pages, (Jul. 30, 1998).

"The Arrhythmia Monotoring System (Heartcard)", http://www.instromedix.com/prodhcl.htm, Istromedix, Inc., 2 Pages, (Jul. 30, 1998).

"The Biolog", http://www.micromed.com.au/products/Biolog, Micromedical Industries Limited, 1 Page, (Jul. 30, 1998).

"The Electrocardiograph", *Biopotential Amplifiers,* Webster, pp. 290–296, (1992).

"The Vet Biolog", http://www.micromed.com.au/products/Veterinary Biolog, Micromedical Industries Limited, 1 Page, (Jul. 30, 1998).

"Universal Active Filter—UAF42", *Burr–Brown Corporation,* pp. 1–6, (Jan., 1998).

"Utilities", http://www.futureone.com/, damaged, Damaged Cybernetics, (2 pages).

Anthrox, P., "Everything You Always Wanted to Know About Game Boy", (Informational Brochure) Nintendo Co., Ltd., 18 Pages.

Fayzullin, M., "gblist.c", http://www.freeflight.com/fms/Gameboy, Copyright Marat Fayzullin, 6 Pages, (1996).

Fayzullin, M., "General Questions About Game Boy", http://www.freeflight.com/fms/GameBoy/General.html, 3 Pages, (Jul. 30, 1998).

Fayzullin, M., "Nintendo Gameboy Frequently Asked Questions", http://www.komkon.org/fms/stuff/gameboy.faq, Nintendo (version 3.1b), 22 Pages, (Aug. 22, 1995).

Fayzullin, M., "Virtual Gameboy", http://ww.komkon.org/fms/VGB, 3 Pages, (Jul. 30, 1998).

Frohwein, J., "Gameboy Op Code Summary", http://www.venom.com.au/gameboy/gbop.txt, 9 pages, (Jul. 30, 1998).

Frohwein, J., "GB Basic FAQs", http://fly.hiwaay.net/, jfrohwei/gameboy/gbbasic.html, (1 Page).

Frohwein, J., "Jeff Frohwein's Game Gene for Game Boy Page", http://fly.hiwaay.net/, jfrohwei/gameboy/gg.html, (1 Page).

Frohwein, J., "Jeff Frohwein's GameBoy Tech Page", http://fly.hiwaay.net/, jfrohwei/gameboy/docs.html, (Hardware Information), (5 Pages).

Frohwein, J., "Jeff Frohwein's Gameboy Tech Page—What's New", http://fly.hiwaay.net/, jfrohwei/gameboy/hardware.html, (3 Pages).

Frohwein, J., "Jeff Frohwein's GameBoy Tech Pate", http://fly.hiwaay.net/, jfrohwei/gameboy/home.html, (Software Information), (5 Pages).

Molina, J., et al., "Filter Design Program For The UAF42 Universal Active Filter", *Burr–Brown Corporation,* Application Bulletin, pp. 1–14, (Jul. 1993).

Moore, D., "Gameboy Authentication Explained", http://www.futureone.com/, damaged/consoles/auth.htm, Damaged Cybernetics, (2 Pages).

Roberts, H.E., "Electrocardiograph", *Radio–Electronics,* pp. 31–47, (Jul. 1991).

Roberts, H.E., "Electrocardiograph", *Radio–Electronics,* pp. 44–49, (Aug. 1991).

Trump, B., et al., "MFB Low–Pass Filter Design Program", *Burr–Brown Corporation,* Application Bulletin, pp. 1–8, (Jul. 1993).

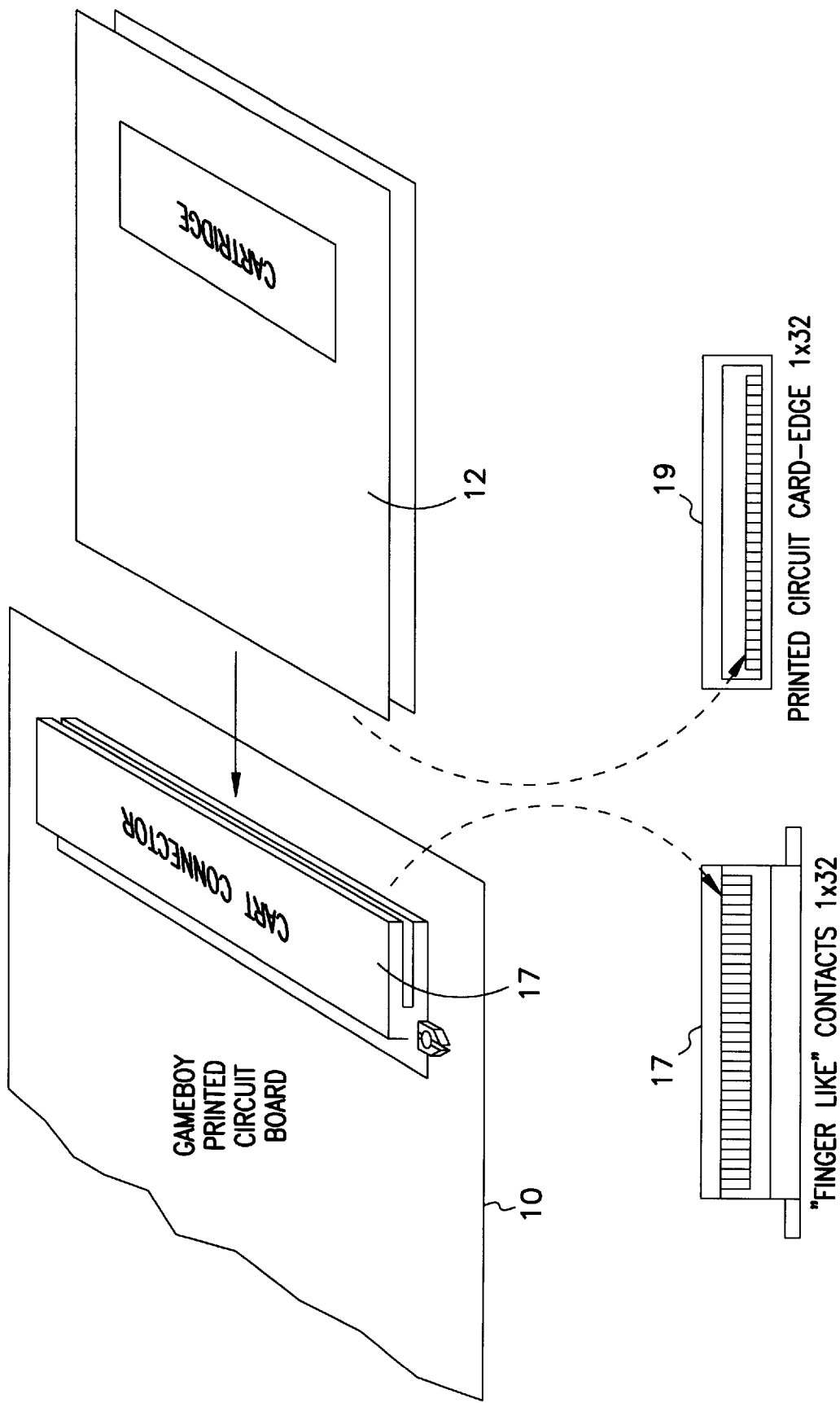

PORTABLE MODULAR DIAGNOSTIC MEDICAL DEVICE

FIELD OF THE INVENTION

This invention relates generally to diagnostic medical devices, and particularly to such devices that are portable and modular.

BACKGROUND OF THE INVENTION

Quality and cost-effectiveness are significant issues in health care. The diagnosis and treatment of a patient by a clinician is the underlying core of the health care process. The clinician, such as a doctor, a nurse, or other medical professional, typically relies upon medical instrumentation to provide objective measurements of the patient that are used to prescribe treatment. The quality and cost of health care, therefore, are directly linked to the quality, availability, and cost of the medical instrumentation utilized.

The criteria typically used to evaluate diagnostic medical instruments include safety, efficacy, and cost-effectiveness. The safety standards are explicitly defined by the Association for the Advancement of Medical Instrumentation (AAMI). For example, the AAMI's safety standards for electrocardiographic (ECG) devices are described in "American National Standard Diagnostic Electrocardiographic Devices," ANSI/AAMI EC11-1991, which is hereby incorporated by reference.

Efficacy and cost-effectiveness, however, are not as clearly defined and depend greatly upon the clinician's needs. For a medical instrument such as an electrocardiogram (ECG) or electroencephalogram (EEG) device, the effectiveness of the device involves not only how well it measures the biopotential in question, but also its ability to provide useful information in a timely, usable, and appropriate manner. Equipment with a poor user interface or inadequate controls, as typically found within the prior art, is unlikely to be used, and not at times when the information needs are time critical. Bulky or heavy equipment, as is also usually the norm within the prior art, cannot be easily moved to remote locations or carried into emergency situation environments.

Conversely, portable equipment found within the prior art such as holter ECG monitors available as the Digitrak Holter Monitor from Zymed, Inc., of Camarillo, Calif., require additional hardware to permit viewing of the stored signal. On-line, real-time diagnosis cannot be made at a remote location with such prior art portable medical diagnostic equipment without telemetry to a base unit or transmission over a telephone line. The patient data needed to make diagnoses quickly and effectively cannot be accessed readily; therefore, the instrumentation fails to meet user needs in a real-time manner.

Cost-effectiveness is also critical to meeting user needs. Inexpensive diagnostic equipment must be accessible to the medical practitioner for application to the end customer—the patient. If requisite diagnostic medical equipment is not available because of budgetary constraints, the quality of health care suffers. The average price of major manufacturer ECG equipment is typically in the $5,000–$10,000 range. Many underfunded clinics within and outside the United States cannot afford basic equipment such as simple ECG machines.

The cost of medical diagnostic equipment is high because, in part, product development costs continue to increase. Each new product typically has its own specific hardware and software. Little common instrumentation architecture is available. Existing solutions within the prior art do not fully overcome these shortcomings.

One prior art approach is the medical data acquisition hardware card, for insertion into and use with a PC-compatible computer. However, computers are still expensive, typically costing upwards of $1,000–$2,000. In the case where a desktop computer is used, the resulting diagnostic medical device is still not portable.

Furthermore, a PC-compatible computer-based approach tends to have high support and installation costs. A given medical hardware card may not run on a given PC-compatible computer without significant user involvement during the installation process, because of differences across such computers. The hardware card usually does not include necessary software built in; the software must itself be separately loaded onto the computer, and thus raises another compatibility concern for a given computer. Computer-wary clinicians may not be likely to trust the computer to provide it with medical diagnoses, and non-computer-savvy clinicians may find using such software as difficult as learning a complex word-processing or spreadsheet program.

Most significantly, the PC-compatible platform may not have the stability that is required of medical diagnostic devices. While the "crashing" of a computer is inconvenient in the situation where a word-processing program is being run on the computer, for example, the crashing of such a computer may literally cause a life-threatening situation where the computer has been transformed into a medical diagnostic device via a hardware card and corresponding software. Ominously, because of the great variability in different PC-compatible platforms, there is no way to guarantee that such crashing will not occur on a particular PC-compatible computer.

Other standard architectures exist to provide the backbone of diagnostic medical devices, such as the EasiView EKG System available from Zymed, Inc., of Camarillo, Calif., and the CardioVoice Phone/System available from Paceart Associates of Wayne, N.J. However, these architectures are themselves typically specific to only diagnostic medical devices. Because the market for such medical devices is much smaller than that for PC-compatible computers, for example, the economies of scale with these standard architectures are still not great enough to permit a markedly great reduction in medical device cost.

Furthermore, the architectures represent only an initial starting point in the development of a diagnostic medical device, around which the architectures are designed. The resulting medical device is not modular. Its designed-for medical functionality cannot be switched out for different medical functionality for use with the same physical instance of the backbone architecture. The medical functionality and the architecture are permanently interconnected and prevent modularity.

Finally, these backbone architectures are typically still PC-compatible based, integrating a PC-compatible motherboard into the architecture. Therefore, many if not all of the shortcomings of utilizing PC-compatible computers as platforms for medical devices carry over to the utilization of these backbone architectures as medical device platforms as well.

SUMMARY OF THE INVENTION

The above-mentioned shortcomings are addressed by the present invention, which will be understood by reading and studying the following specification. The invention describes a portable modular diagnostic medical device. Preferably, the medical device is based on a portable multipurpose computerized platform designed primarily for playing video games. A medical component is removably connected to the platform, and has specialized circuitry specific to a predetermined diagnostic medical function. In a preferred embodiment, the platform is a Nintendo Gameboy video game device, and the medical component is a cartridge that plugs into the Gameboy device.

The resulting diagnostic medical device addresses all the shortcomings described above. It is a low-cost, mass-produced, portable hand-held device having features including an integrated screen, user-friendly controls, and a serial port. Clinicians can take this light, portable instrumentation device to a remote location very easily. The device is easy to operate, since it is based on a video game system relatively simpler than a PC-compatible computer. Different diagnostic medical functionality is achieved by inserting different cartridges into the device. A particular diagnostic medical functionality is preferably self-contained within a given cartridge.

In different embodiments of the invention, medical devices, components and cartridges of varying scope are described. Still other and further aspects, advantages and embodiments of the invention will become apparent by reference to the drawings and by reading the following detailed description.

BRIEF DESCRIPTION OF THE DRAWINGS

FIG. 2(b) is a diagram showing the insertion of an ECG cartridge into the platform of FIG. 2(a);

DETAILED DESCRIPTION OF THE INVENTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the appended claims.

Overview of the Preferred Embodiment

In a preferred embodiment of the invention, a portable modular diagnostic medical device is described that is based upon a NINTENDO GAMEBOY video game system platform, and that monitors electrocardiogram (ECG) signals. The NINTENDO GAMEBOY device platform is manufactured and sold by Nintendo Co. Ltd., of Kyoto, Japan, through its American affiliate, Nintendo of America, Inc., of Redmond, Wash. The invention, however, is not so limited. That is, the invention is not limited to implementation utilizing a NINTENDO GAMEBOY device platform. Furthermore, the invention is not limited to diagnostic medical functionality including the measurement of ECG signals.

The measurement of ECG signals is of great utility in the practice of medicine, and is known within the art. For example, the reference Polnsey and Barr, Bioelectricity: A Quantitative Approach (1988), which is hereby incorporated by reference, provides a general description of ECG signals and their diagnostic medical utility. ECG signals correspond to the beating of a heart. As the heart pumps blood, it generates electrical signals. These signals can be measured from a number of different vantage points by the connection of leads onto different parts of the host body via electrodes. From different vantage points, medical conditions such as arrhythmia, fibrillation, and high blood pressure can be properly diagnosed, and therefore treated.

Figure 1:
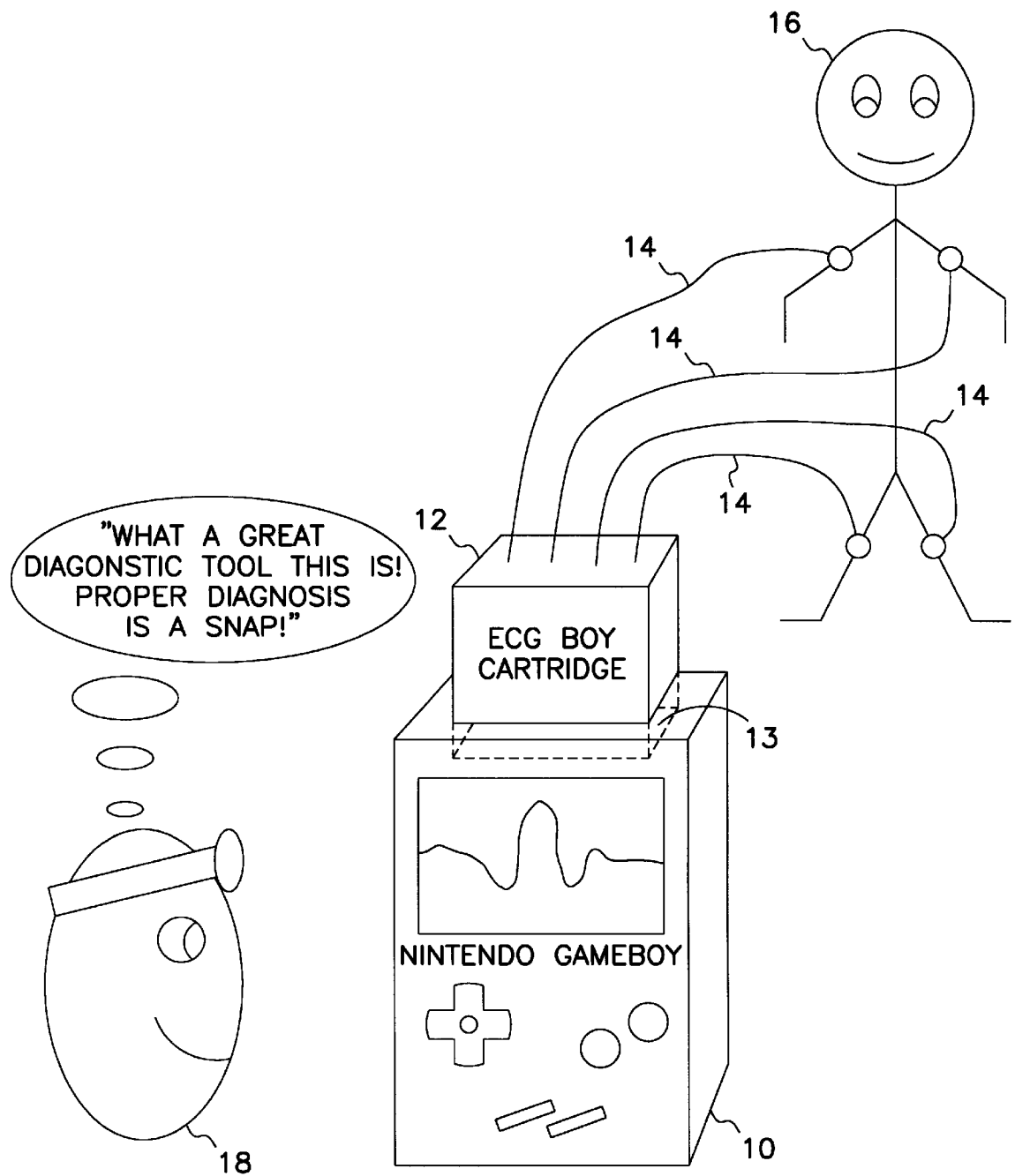
FIG. 1 is a diagram of the utilization of a portable ECG device according to a preferred embodiment.

Referring to FIG. 1, a diagram of the utilization of a portable ECG device according to a preferred embodiment is shown. Platform 10 has removably inserted therein medical device cartridge 12 (into a corresponding slot 13), from which a plurality of optically isolated leads 14 extrude. The plurality of leads 14 are attached to different locations on host body 16 via disposable self-adhesive electrodes, as desired by the clinician to view ECG signals from particular vantage points. Cartridge 12 preferably includes integrated software and specialized circuitry specific to the monitoring of ECG signals, and enclosed within a housing. Other cartridges 12 for removable insertion into platform 10 and that perform different diagnostic medical functions are contemplated. Via a cartridge 12, the platform 10 is transformed into a diagnostic tool.

ECG signals from host body 16 are measured by cartridge 12 and are viewable on a screen of platform 10 by clinician 18. As shown in FIG. 1, host body 16 is a human patient. The invention is amenable to use on other host bodies, such as animals. Because of the power requirements of cartridge 12, it typically includes a small external battery pack not shown in FIG. 1. Therefore, cartridge 12 is slightly larger in size than a typical video game cartridge that does not otherwise use external power.

The configuration shown in FIG. 1 provides the clinician with a diagnostic medical device having functionality as programmed in cartridge 12. The interface between the clinician and the device is through platform 10. Platform 10 provides a display upon which diagnostic medical information can be viewed. The specific medical functionality's options and controls are selected via platform 10 as well. The actual integrated software and specialized circuitry to transform platform 10 into a diagnostic medical tool, however, is provided by cartridge 12.

Figure 2A:
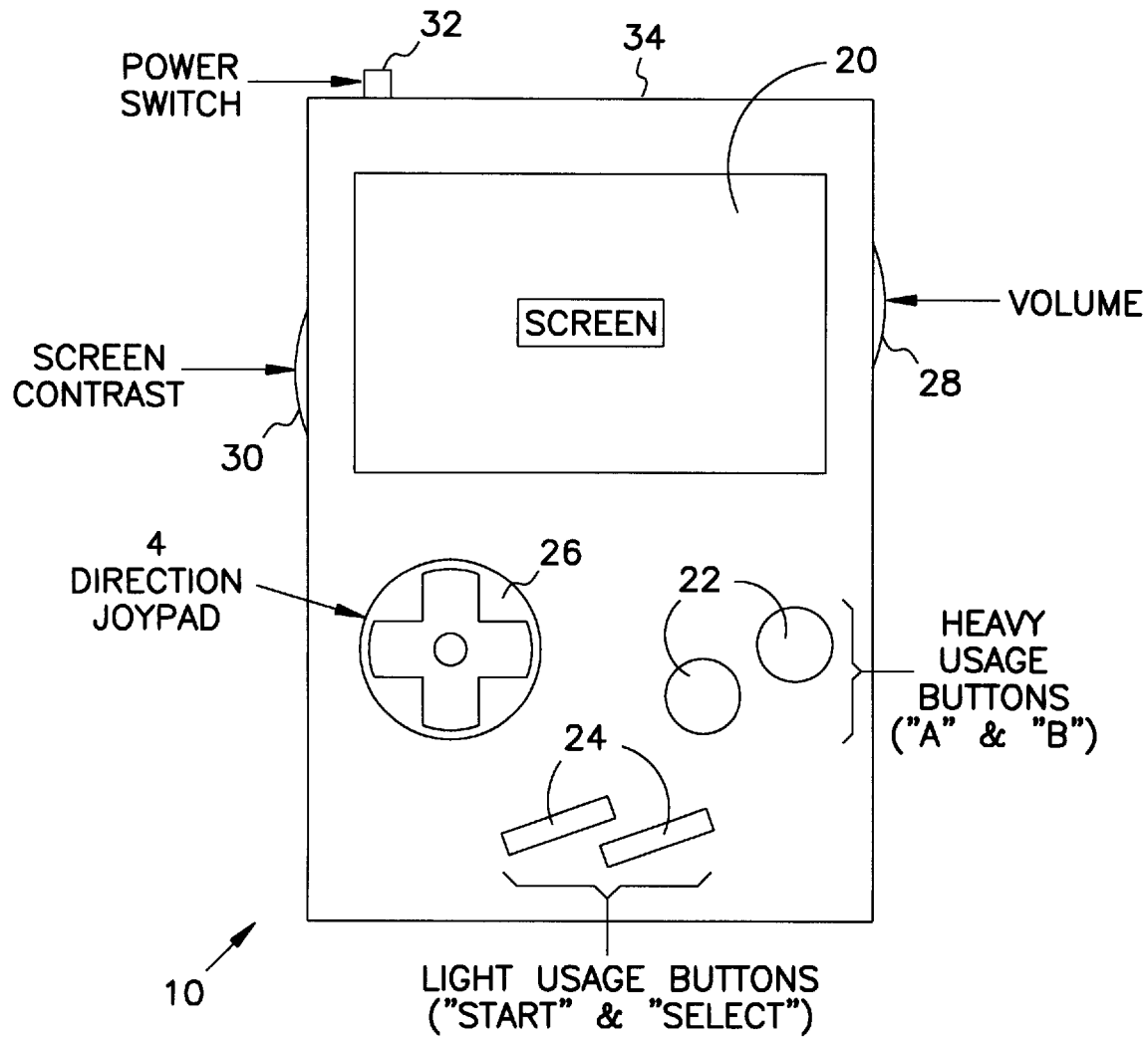
FIG. 2(a) is a diagram showing the platform of FIG. 1 in greater detail.

Referring now to FIG. 2(a), a diagram of platform 10 of FIG. 1 is shown in more detail. Platform 10 is a NINTENDO GAMEBOY device platform, as has been described. The NINTENDO GAMEBOY device platform is a well-known platform designed for the playing of video games. The NINTENDO GAMEBOY device is a lightweight, inexpensive and portable platform. It is believed that the NINTENDO GAMEBOY device is the commercial embodiment of the video game system described in U.S. Pat. Nos. 5,184,830, and 5,095,798, both issued to Oakada et al., and both of which are hereby incorporated by reference. The specification herein enables one of ordinary skill within the art to build an ECG-monitoring cartridge that plugs into the NINTENDO GAMEBOY device.

As shown in FIG. 2(a), platform 10 includes display screen 20, which is a 160×144 pixel liquid crystal display (LCD) gray-scale screen, and permits viewing of the measured ECG signals. Control buttons 22 and 24, as well as joypad 26, permit selection from a number of provided options shown as on-screen menus on screen 20. Volume control 28 controls the volume of the sound emanating from headphones attached to a headphone jack of the NINTENDO GAMEBOY device, or from a speaker internal to the device, both of which are not shown in FIG. 2(a). Screen contrast control 30 controls the contrast of display screen 20. Power switch 32 turns the NINTENDO GAMEBOY device on and off. Cartridges are attached to the NINTENDO GAMEBOY device via an unshown slot within the device's top surface 34. Also not shown in FIG. 2(a) is that the NINTENDO GAMEBOY device includes an alternating current (AC) adapter jack, to permit AC operation, and a serial port. Furthermore, the Gameboy device includes a processor and read-only memory (ROM), also not shown in FIG. 2(a).

The NINTENDO GAMEBOY device has been chosen as the platform upon which a preferred embodiment is based because of a number of its features that are desirable or useful in a medical diagnostic tool. The NINTENDO GAMEBOY device is handheld, lightweight, and portable (viz., it is battery powered using AA batteries). The NINTENDO GAMEBOY device is inexpensive. It is believed that such devices as of the filing date of this application are available for approximately fifty dollars. The need for reasonable quality graphic and sound capabilities, adequate computer speed (required for complex games), flexibility in programming for a plethora of games, and networkability, has driven video game manufacturers such as Nintendo to develop and market platforms with considerable capability at very low cost, such as the NINTENDO GAMEBOY device.

In a preferred embodiment of the invention, the ECG-monitoring device is event driven and scans for movement on the joypad of the NINTENDO GAMEBOY device during normal execution. The select control 24 is used to toggle the lead signal that is digitized and plotted on the screen, such as lead I, II, or III, or CAL. The CAL signal is a one millivolt test reference used to calibrate the display and confirm that the unit is working properly. The left and right arrow keys on the joypad are used to change the total amount of time displayed on the screen (viz., a scale factor, as described hereafter). The joypad is also used to select menu items listed along the bottom of the screen.

Referring to FIG. 2(b), a diagram showing the insertion of an ECG cartridge into a NINTENDO GAMEBOY device is shown. NINTENDO GAMEBOY platform (a type of cartridge-based portable video game system platform) 10 is shown without its housing. It includes a cartridge connector 17. Cartridge 12 plugs into platform 10. That is, cartridge 12 includes a corresponding connector 19 that fits into connector 17. As shown, connector 19 is partially disposed within the housing of cartridge 12; the connector 19 is obviously revealed sufficient to permit it to connect to connector 17. Furthermore, connector 17 of platform 10 when the housing of platform 10 is installed is disposed at the bottom of a slot within the housing (e.g., the slot 13 as shown in FIG. 1).

Figure 3A:
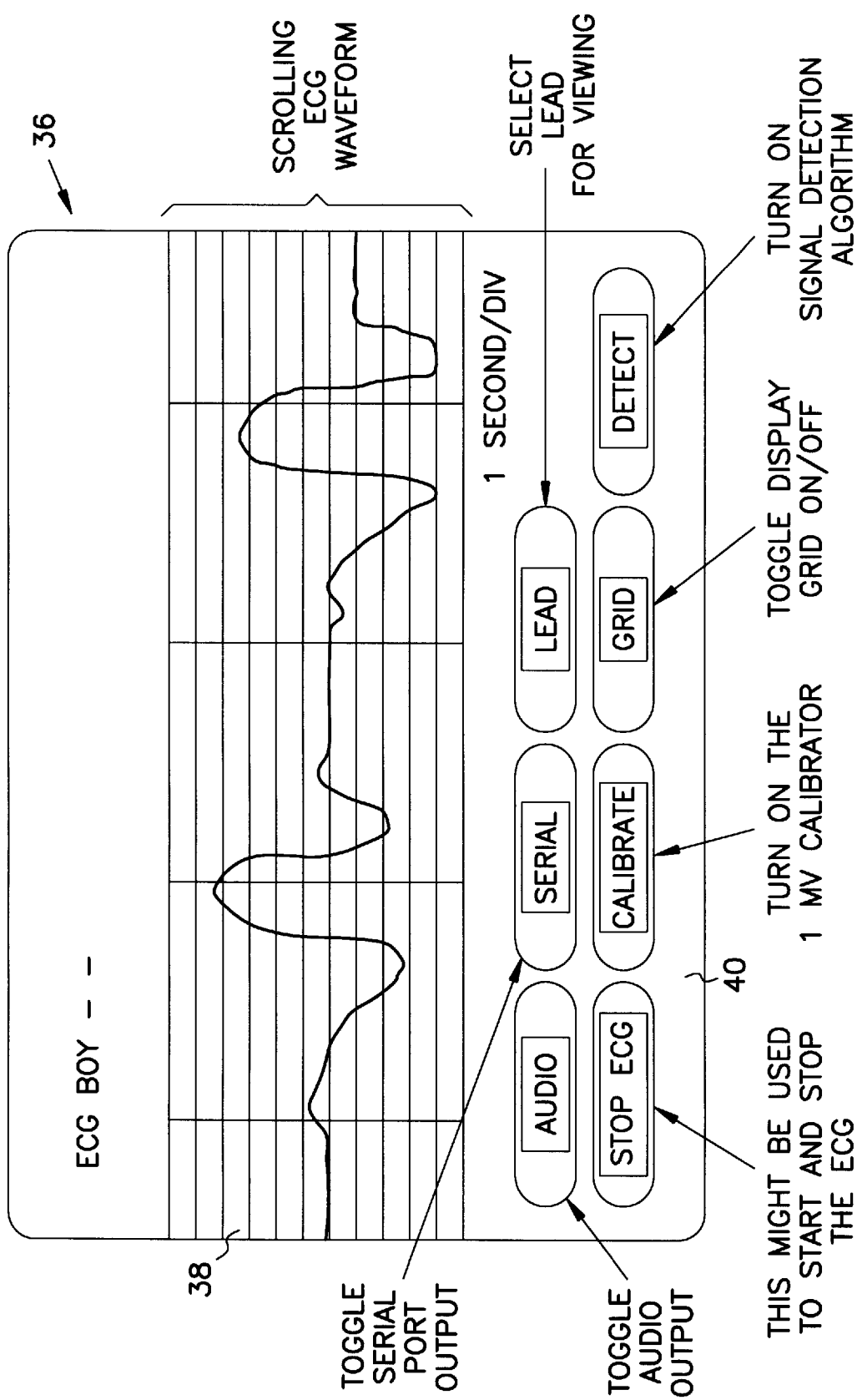
FIG. 3(a) is a screen output of an ECG monitoring device according to one embodiment of the invention.

Referring to FIG. 3(a), a contemplated screen output of an ECG monitoring device according to one embodiment of the invention is shown. Screen output 36 is displayed on the screen of a platform utilized by the invention. Controls 40 are selected using the joypad and control buttons of the platform. An actual scrolling ECG waveform is displayed against a grid in area 38 (i.e., a single channel real-time ECG in gray scale); alternatively, an ECG waveform is displayed against the grid, and when the entire grid is occupied, the waveform is erased, and a new section of the waveform is displayed. The waveform shown in area 38 corresponds to a particular lead that has been attached to a host body. Selecting the lead control 40 changes the ECG waveform viewed in area 38. The grid against which the ECG waveform is displayed is toggled on and off via the grid control 40.

Amplitude calibration of the ECG waveform against a one millivolt (mV) reference is accomplished via selection of the calibrate control 40. Selection of detect control 40 turns on the signal detection algorithm; that is, selection of detect control 40 causes an ECG waveform to be displayed in area 38. Selection of stop ECG control 40 turns off the scrolling of the waveform (i.e., stopping the detection of the ECG waveform selected by the lead control 40). The waveform is additionally output to the serial port of the platform by toggling serial control 40, and is output as an audio signal to the internal speaker or headphones attached to the headphone jack by toggling audio control 40.

As shown in FIG. 3(a), the ECG monitoring device according to a preferred embodiment of the invention is a full-featured ECG device. The clinician is able to select an ECG signal from any of a number of different leads. Outputting of the signal via the serial port permits the acquired data to be sent via cable to a local laptop computer or smart modem. Outputting of the signal on the speaker or through the headphones may enhance data visualization for the clinician; the speaker can also be used as an acoustic modem to transmit the signal from a remote location to a hospital via a normal phone connection. Finally, now shown in FIG. 3(a) is that the battery back-up of the ECG waveforms stored in memory can permit the user to store sampled waveforms for later viewing and diagnosis.

Figure 3B:
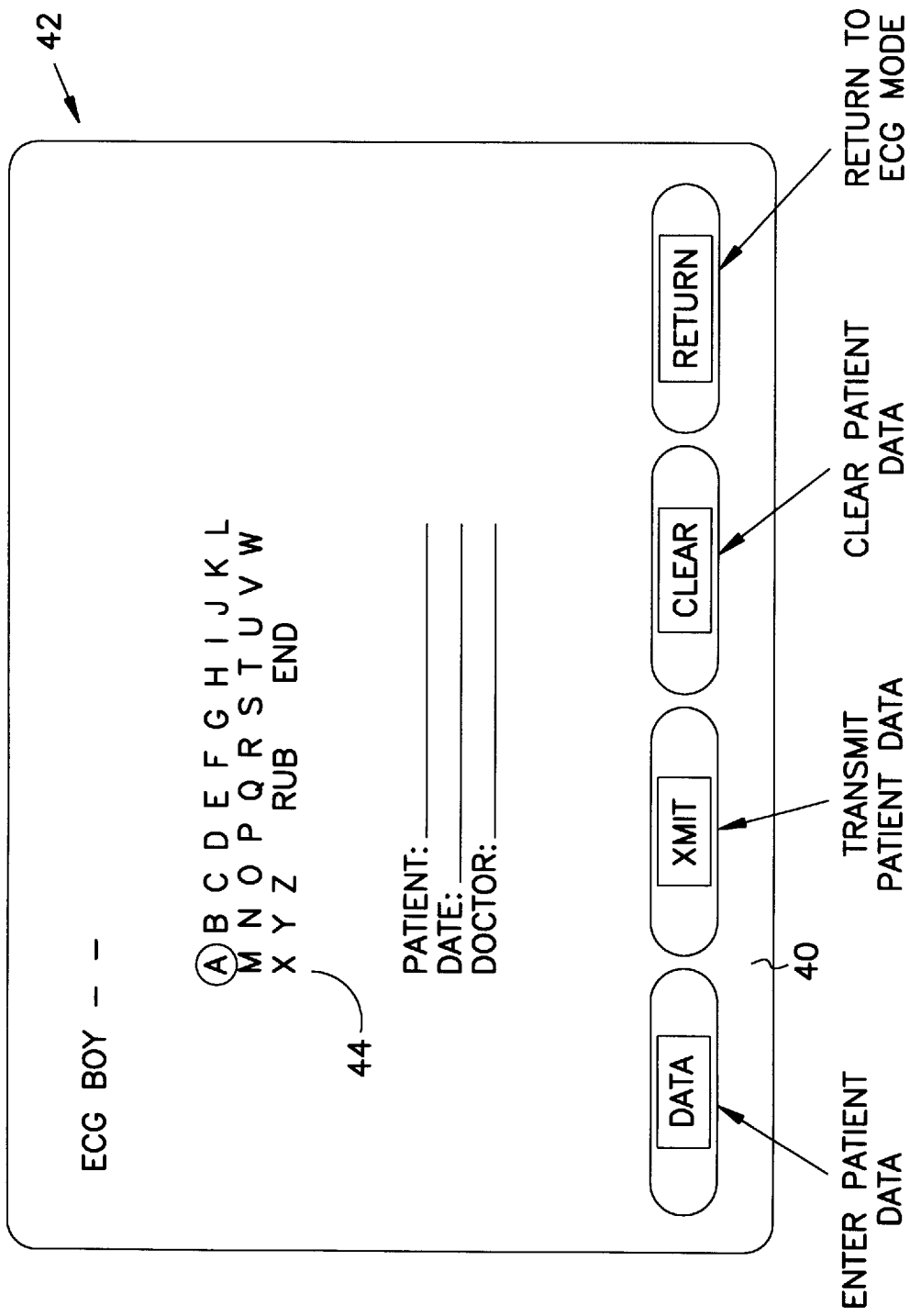
FIG. 3(b) is a further screen output of an ECG monitoring device according to one embodiment of the invention.

Referring next to FIG. 3(b), a further contemplated screen output of an ECG monitoring device according to one embodiment of the invention is shown. Screen output 42 is displayed on the screen of the platform used by the invention. Within screen output 42, the user of the device is able to label particular sampled waveforms with information regarding the host body from which they came. This is accomplished through text entry area 44 and controls 46. Because the Gameboy device does not include a computer, text is entered by selecting a letter within area 44 via the joypad and controls of the NINTENDO GAMEBOY device.

Controls 46 are also selected using the joypad and controls of the NINTENDO GAMEBOY device. Data control 46 permits such entry of text information. Once entered, data control 46 permits the transmittal of this information (i.e., the saving of this information), while clear control 46 clears the entered information, and return control 46 returns the user to the screen output shown in FIG. 3(a).

Hardware Implementation: Analog Section

Figure 4:
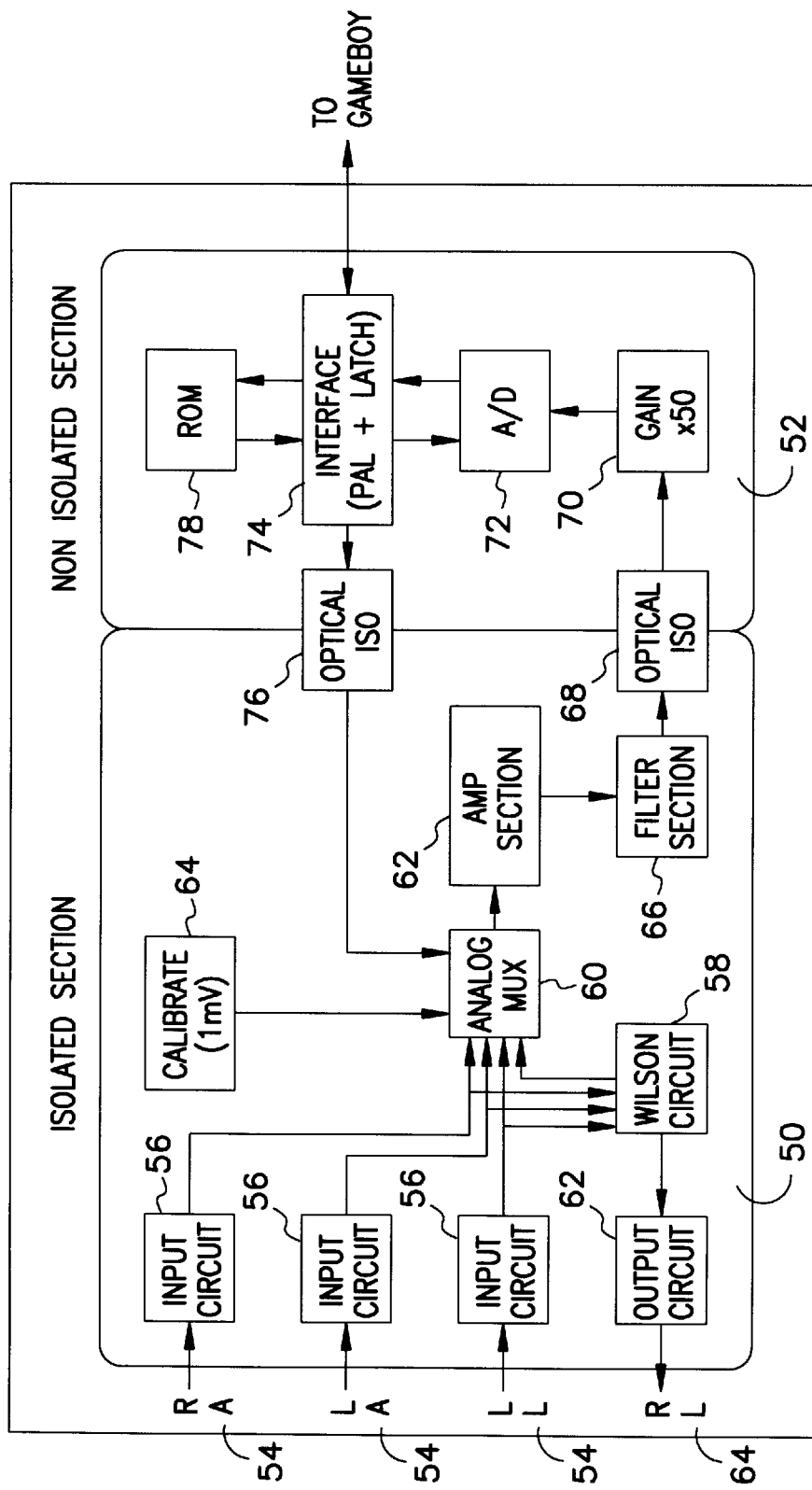
FIG. 4 is a block diagram of an ECG-monitoring diagnostic medical device cartridge for removable insertion into a computerized platform according to a preferred embodiment of the invention.

Referring to FIG. 4, a block diagram of an ECG-monitoring diagnostic medical device cartridge for removable insertion into a computerized platform according to a preferred embodiment of the invention is shown. Cartridge 48 is designed as shown in FIG. 4 for insertion into a NINTENDO GAMEBOY platform (a type of cartridge-based portable video game system platform). Cartridge 48 includes optically isolated section 50 and non-optically isolated section 52. This section of the specification describes an analog section of the cartridge, which includes all the components within isolated section 50, and gain amplifier 70 of non-isolated section 52. The next section of the specification describes a digital section of the cartridge, which includes all the other components within non-isolated section 52. The analog section of the cartridge performs the actual ECG-monitoring functionality of the cartridge of FIG. 4; the digital section converts the ECG signals measured into a digital format for display by the NINTENDO GAMEBOY device, interfaces the NINTENDO GAMEBOY device to a read-only memory (ROM), and controls the measurement of the ECG signals by the analog section.

Leads 54, for the right arm (RA) or shoulder, left arm (LA) or shoulder, and the left leg (LL), are connected to input circuits 56. Leads 54 are standard ECG leads as has already been described; they connect to electrodes placed on the indicated areas of a host body (i.e., RA lead connected to an electrode placed on the right arm or shoulder of the host body, etc.). Each input circuit 56 includes an overvoltage protection circuit and buffer amplifiers, as known within the art.

Preferably, the over-voltage circuitry is implemented utilizing a pair of silicon diodes connected in parallel and oriented in opposite directions. The overvoltage circuitry limits the potential that can occur on the host body with respect to the input ground. Any lead voltage of a magnitude exceeding about 600 millivolts (mV) will forward bias a diode and be grounded out. This in turn limits the current passed through the patient.

Preferably, each buffer amplifier includes one buffer op amp (such as an LF441A op amp) configured as a voltage follower. This provides a good high impedance interface between the patient and the device, and again limits the current passed through the patient. Additionally, the voltage follower provides the current necessary to drive the next stage of the analog section while preserving the measured biopotentials at the leads.

The signals are passed from input circuits 56 to Wilson circuit 58, and analog multiplexing circuit 60. Wilson circuit 58 is used to form the Wilson electrode, a standard reference for potential measurements from the three leads 54. It is common design practice in ECG-monitor devices to utilize the Wilson electrode to reduce noise in the measured signals. The Wilson circuit includes one op amp that sums the signals from each of input circuits 56, and another op amp to invert and amplify the summed signal, which is then fed back through output circuit 62, to right leg (RL) lead 64, to which an electrode attached to the right leg of the host body is connected. The summed signal is the common mode voltage occurring on the body, and is inverted, amplified and fed back to the host body in order to reduce common mode noise. The summed, inverted, and amplified signal is also sent to the multiplexing circuit 60. The Wilson circuit arrangement utilized in this preferred embodiment is commonly known as a driven right leg system.

Preferably, Wilson circuit 58 includes one amp to weightedly sum the signals from input circuits 56 (e.g., a ¼ LM348 op amp, although the invention is not so limited), and another op amp configured as an inverted amplifier to amplify the summed signal and restore the original phase of the summed signal prior to sending the summed signal to output circuit 62 and multiplexing circuit 60 (e.g., a ¼ LM348 op amp, although the invention is not so limited). (That is, the op amp summer inverts the phase of the signals from the input circuits in the process of summing them.) Like the input circuits 56, output circuit 62 includes a pair of overvoltage protection diodes to protect the host body from over-voltage conditions. The diodes are configured in parallel and oriented in opposite directions, like the diodes of the input circuits 56.

Those of ordinary skill within the art typically expect an adjustable offset circuit to also feed into the analog multiplexing circuit, besides the outputs of the input circuits 56 and the Wilson circuit 58. For example, a digital-to-analog converter may be used to individually correct direct current (DC) offsets for each channel (viz., the output of each input circuit). In the interests of simplicity and minimization of components, however, the preferred embodiment does not include such an adjustable offset circuit. It is believed that the differential nature of the amplifier section 62 itself, by rejecting common mode signals, is sufficient to correct for DC circuit errors.

Analog multiplexing circuit 60 is used to switch the inputs to the subsequent amplification stage (viz., amplifier section 62). Preferably, analog multiplexing circuit 62 includes a dual four analog multiplexer (e.g., a Max309 mux) that switches the desired two leads for input to the amplifier section 62, and a second multiplexer (e.g., a Max333A mux) that switches the desired reference against which each of the desired two leads is differentially amplified in a first stage of the amplifier section 62 (e.g., either ground, or the Wilson reference). Both multiplexers are controlled by the digital section, as is described later. The Max multiplexes are manufactured by and available from Maxim Integrated Products, Inc., of Sunnyvale, Calif.

Figure 5:
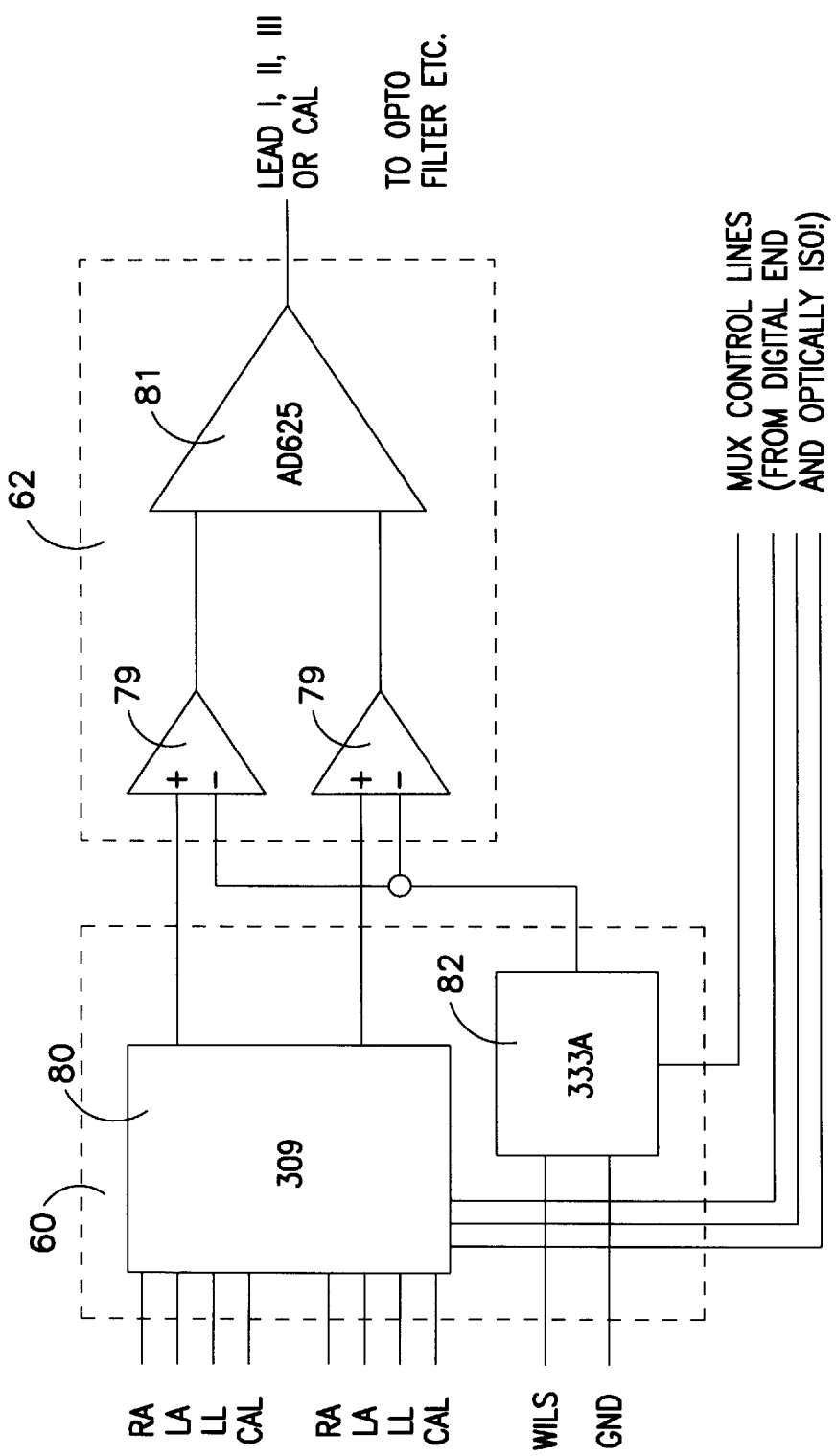
FIG. 5 is a diagram of the analog multiplexing circuit and the amplifier section of FIG. 4 in more detail.

A more detailed view of analog multiplexing circuit 60 is shown in FIG. 5. Dual four analog multiplexer 82 is used to select among the three limb signals from input circuits 56, and also a one millivolt calibration signal from calibration circuit 64 (not shown in FIG. 5), the construction of which is known within the art. Multiplexer 80 requires three control lines, to select the inputs to switch to the output. The two outputs of multiplexer 80 are the desired inputs to the amplifier section. That is, the circuit is designed to switch RA and LA (lead I), RA and LL (lead II), and LA and LL (lead III). Furthermore, the circuit is design to switch any of the limb signals with the one millivolt calibration signal from calibration circuit 64. The calibration signal may also be paired against ground. Preferably, four different output states are contemplated:

| State | First Output | Second Output |
| --- | --- | --- |
| 1 | Right Arm | Left Arm |
| 2 | Left Arm | Left Leg |

-continued

| State | First Output | Second Output |
|---|---|---|
| 3 | Right Arm | Left Leg |
| 4 | Cal | Ground |

Multiplexer 82 switches between ground and the Wilson reference provided by Wilson circuit 58 of FIG. 4. The output of multiplexer 82 is also fed as an input to the amplifier section. As will now be described, the output of multiplexer 82 serves as a reference signal against which each output of multiplexer 80 is first differentially amplified, before being differentially amplified against one another. This serves to ensure a clean signal.

Referring back to FIG. 4, the two outputs of analog multiplexing circuit 60 are inputted to amplifier section 62. Each limb signal is amplified with respect to another, thereby creating a lead, such as lead I, lead II, or lead III, as has already been described. These leads are not to be confused with leads 54 that have also already been described. The gain is preferably set to 1000 via external resistors, as known within the art. However, computer-controlled gain is also contemplated. The gain is differential in that it amplifies the differential biopotential between the two inputs provided by multiplexing circuit 60, as differentially amplified with a reference signal. Therefore, common mode signals are rejected.

The amplifier section 62 is construed using at least an AD625 integrated circuit. It is believed that this is a relatively expensive circuit. However, it is crucial that the amplifier section has good common mode signal rejection characteristics. The AD625 integrated circuit is an instrumentation amplifier that has a minimum common mode rejection of 110 dB at a gain of 1000. A more detailed view of a preferred embodiment of amplifier section 62 is also shown in FIG. 5. Each output of mux 80 is first differentially amplified against a reference that is the output of mux 82 via an amplifier 79. The output of each amplifier 79 is then output to amplifier 81, which is the AD625 amplifier as has been described.

Referring back to FIG. 4, the amplified signal from amplifier section 62 is passed to filter section 66. Filter section 66 is a two-pole Chebychev filter having a high-pass segment with a cutoff frequency of 0.01 Hz, and a low-pass segment at 100 Hz. That is, the amplified signal from amplifier 62 is filtered such that only frequencies from 0.01–100 Hz are passed. Design and implementation of this filter preferably utilizes Burr Brown UAF42 universal filter chips and associated software, available from the Burr-Brown Corp. of Tucson, Ariz., and as described in the specification sheet "Universal Active Filter," available from the Burr-Brown Corp. as specification sheet PDS-1070F (1993), and as also described in the reference S. Molina, "Filter Design Program for the UAF42 Universal Active Filter," available from the Burr-Brown Corp. as AB-035 (1991), both of which are hereby incorporated by reference.

It is believed that the preferred embodiment as described meets AAMI/ANSI ECG recommended safety standards. Furthermore, only contemplated design changes to the Chebychev filter are believed to be necessary to being the device into compliance with the AAMI/ANSI ECG recommended frequency response standards. Specifically, the filters as described have been designed around rough physiological values, whereas the AAMI/ANSI ECG standards cite studies that find a low end of 0.67 Hz and a higher end of 150 Hz are better suited for a diagnostic ECG. Also, the AAMI/ANSI ECG standards require a frequency response test with less ripple in the pass band than that which is achievable using the described filter. A two dB reduction in pass band ripple is required to meet the AAMI/ANSI ECG standards. As known within the art, because the filters described are Chebychev filters, less ripple in the pass band results in a less sharp frequency cutoff. However, it is believed that it is possible to reduce the ripple while still maintaining reasonable roll off, using Chebychev filters.

Optical isolator 68 optically isolates the filtered signal from filter section 66 to gain amplifier 70. A standard 4N26 photo transistor optocoupler is preferably utilized. The battery-driven nature of the NINTENDO GAMEBOY device in actuality reduces drastically the need for optical isolation; however, the ability to use a power line-connected "battery-replacing" transformer (viz., an AC adapter) forces use of isolation techniques. Note that optical isolators 76 optically isolate the six control signals received from the NINTENDO GAMEBOY device through interface 74 to multiplexer 60, and are identical in implementation to the single optical isolator 68. (While a standard single-channel 4N26 optocoupler is used for isolators 68 and 76, it is contemplated that the use of newer integrated circuits having four or eight channels in a single package can be used to reduce real estate usage and power consumption.)

The 4N26 optocoupler results in an attenuation of the filtered signal from filter section 66, however. Therefore, prior to passage of analog to digital converter 72 of the digital section, described in the next section, gain amplifier 70 corrects the attenuation by introducing a gain of 50 to the signal. A pair of inverting amplifier stages is preferably used to construct the amplifier 70. In addition, the signal is centered at 2.5 volts to center the signal within the A/D digitizing range of converter 72. Because the converter 72 preferably has unipolar operation, the number of external components used in amplifier 70 is reduced.

Hardware Implementation: Digital Section

As has been described, the digital section of the cartridge shown in FIG. 4 converts the ECG signals measured by the analog section into a digital format for display by the NINTENDO GAMEBOY device, interfaces a read-only memory (ROM) to the NINTENDO GAMEBOY device, and controls the measurement of the signals by the analog section. The digital section of the cartridge includes analog to digital converter 72, interface 74, and read-only memory (ROM) 78. The hardware implementation of the digital section described herein is pursuant to a currently contemplated preferred embodiment; it is believed that other embodiments are also possible to effectuate the same functionality as is described.

Analog to digital (A/D) converter 72 digitizes the analog ECG waveform. An eight-bit microprocessor-compatible A/D converter is used (e.g., a Maxim 160). However, it is believed that the Maxim 160 is a relatively expensive component, and that a less costly part would suffice. The Maxim 160 has a number of advantageous features. Specifically, the Maxim 160 also uses an external capacitor and resistor to set its conversion rate, which here is approximately ten microseconds maximum conversion time.

The Maxim 160 also features a three-mode microprocessor compatible interface. The three modes are known within the art, and described in the reference "Maxim 160 Microprocessor Compatible 8-Bit A/D Converter" specification sheet available from Maxim Integrated Products, Inc., of Sunnyvale, Calif., and which is hereby incorporated by reference. The static RAM mode is utilized, and allows the microprocessor to initiate conversion with a simple write signal; the data is read using a simple read signal. Specifically, a CHIP_SELECT signal toggling begins the conversion. When the conversion is finished, the combined CHIP_SELECT and READ signals cause the digital value to be placed on the data bus. That is, toggling of the CHIP_SELECT and the READ signals causes the digital value to be placed on the data bus so that it may be read.

Because it is believed that the NINTENDO GAMEBOY device cartridge port does not provide a hardware interrupt, the A/D converter is configured to make each individual conversion as quickly as possible based on its internal clock rate. In this way, the computer can initiate a conversion, wait for a specified length of time exceeding the conversion, and then read the converter; no feedback is required. Specifically, the preferred sequence for digitizing a value is:

1. Write to any address in the start_conversion region to initiate conversion;

2. Wait 3.4 milliseconds; and,

3. Read from any address in the read_conversion region. By initiating each A/D conversion with the appropriate time delay, a sampling rate of 300 Hz is easily maintained for any lead with very little distortion.

Figure 6:
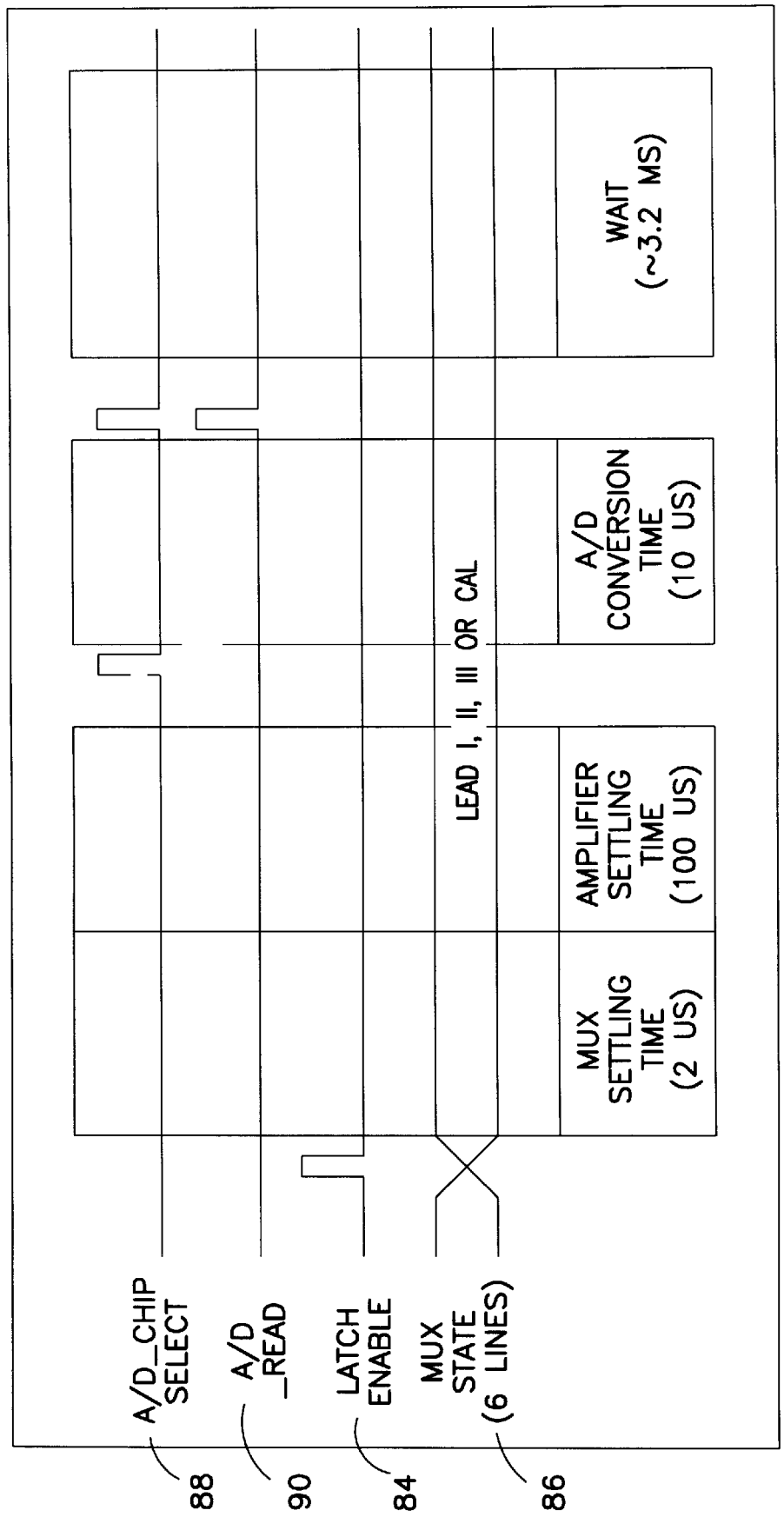
FIG. 6 is a timing diagram for the operation of the analog-to-digital converter in conjunction with the analog multiplexing circuit and the amplifier section, all of FIG. 4.

Referring to FIG. 6, a timing diagram for the operation of the A/D converter in conjunction with the analog multiplexing circuit and the amplifier section is shown. Latch enable 84 (as is more specifically described hereafter) is first momentarily asserted high to force an output of the multiplexer, as selected by the input lines 86. As shown, two microseconds are allowed for the multiplexer to settle. As also shown, an additional one-hundred microseconds are allowed for the amplifier section to settle. The CHIP_SELECT 88 of the A/D converter is next momentarily asserted to initiate an AID conversion, for which ten microseconds are allowed. The CHIP_SELECT 88 and the READ 90 inputs of the A/D converter are then both momentarily asserted to initiate a full read of the digitally converted values of the ECG waveform. After a waiting period of at least 3.4 milliseconds, these values are available for reading on the output bus of the A/D converter.

Referring back to FIG. 4, the converted ECG waveform signals are outputted by converter 72 to interface 74. Interface 74 preferably includes an octal latch (e.g., a 74LS373), along with a standard 22V10PAL custom programmed integrated circuit to interface the NINTENDO GAMEBOY device to ROM 78, A/D converter 72, and analog multiplexing circuit 60 through the latch and optical isolators 76. While a 22V10 PAL is used, the invention is not so limited, and any suitable PLD (programmable logic device) is amenable.

Figure 7:
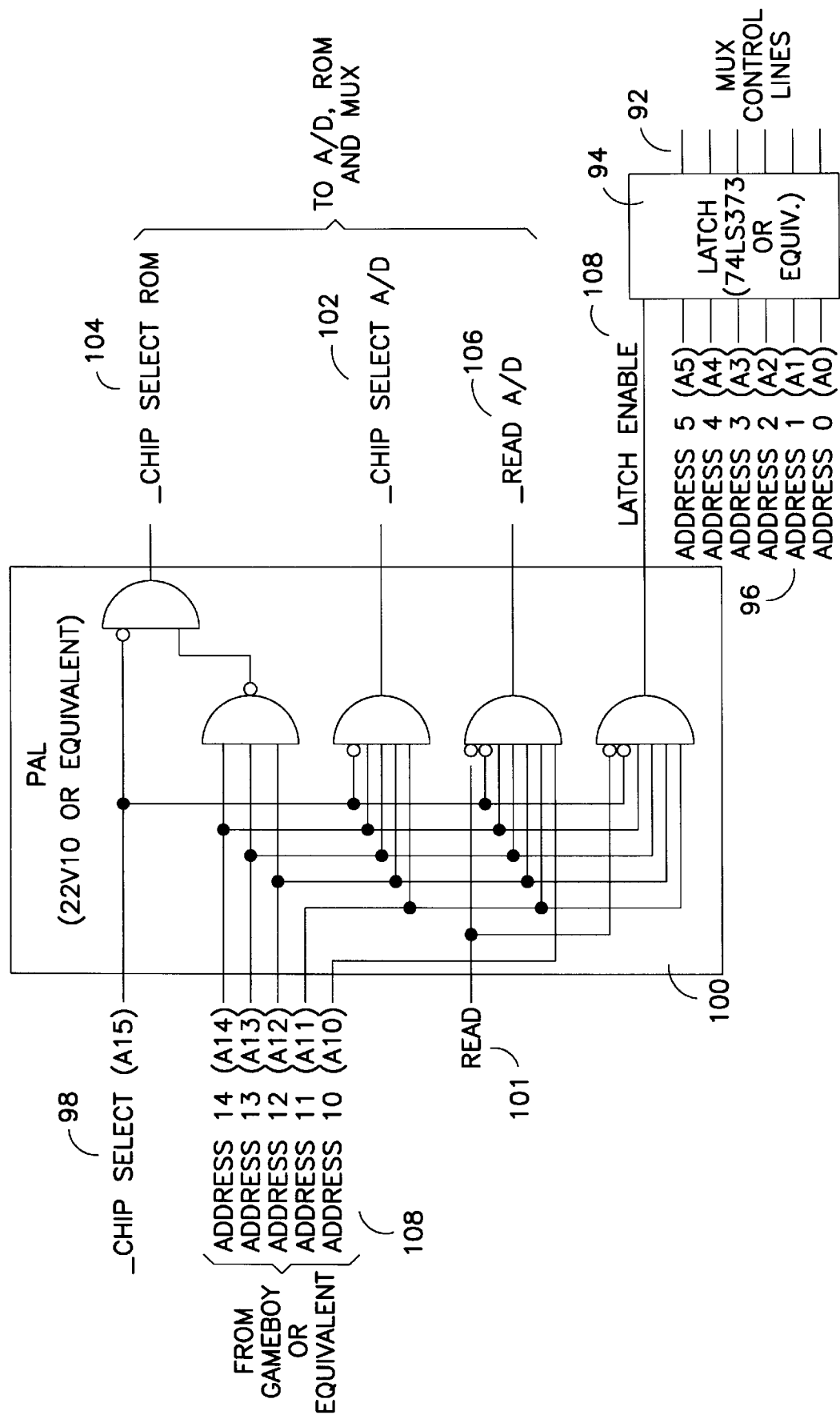
FIG. 7 is a function diagram of the digital interface provided by the interface of FIG. 4.

A function diagram of the digital interface provided by the PAL (programmable array logic) and the octal latch is shown in FIG. 7. Referring to FIG. 7, the six register outputs 92 correspond to analog multiplexer control settings. The octal latch 94 stores the lower address lines 96, for use as multiplexer control lines 92. The control state of each of the multiplexers control lines is placed on the NINTENDO GAMEBOY device bus at A0–A5 (lines 96 in FIG. 7), and the latch enable line 108 is toggled active by the PAL 100 for a short time for latch 94 to take the information. On the inactivating edge of the latch enable line signal, the lowest address lines A0–A5 (lines 96 in FIG. 7) are latched into the registers. The multiplexer control lines 92 are held in the state defined by this data until the latch enable line 108 is toggled again by the PAL 100. Note that latch enable 108 is the latch enable 84 shown in and described in conjunction with FIG. 6; furthermore, the registers output 92 are the mux state lines 86 shown in and described in conjunction with FIG. 6.

The PAL 100 of FIG. 7 is therefore used to control the multiplexer control lines loading into the latch 94; it is also used to partition the memory and handle the control lines of the A/D, ROM, etc. As shown in FIG. 7, the PAL 100 includes logic to map address lines 108, the read line 101, and the chip select line 98 to ROM chip_select 104, A/D chip select 106 (i.e., CHIP_SELECT 88 of FIG. 6), A/D read 106 (i.e., READ 90 of FIG. 6), and latch enable line 108. Depending on the address as asserted on address lines 108 and chip select line 98 (which is the A15 line to the A10–A14 lines of address lines 108), as well as the read line 101, one or more of lines 102, 104, 106 and 108 are asserted.

Figure 8:
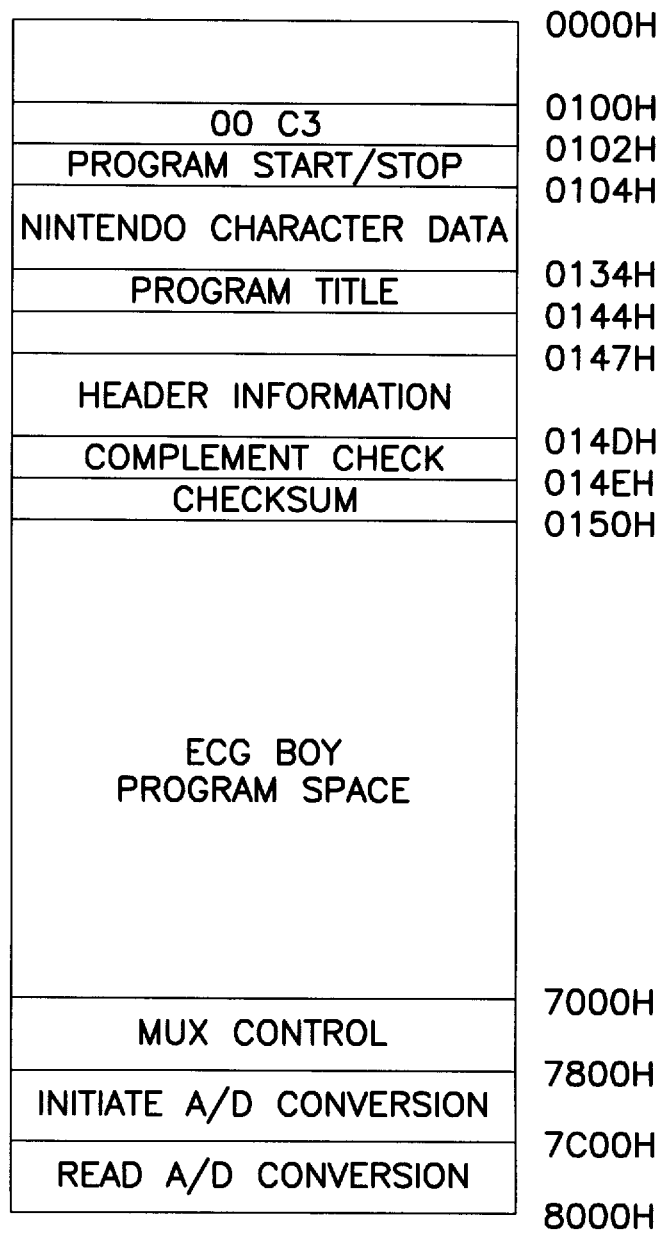
FIG. 8 is a memory map of an ECG-monitoring device, according to a preferred embodiment of the invention; and, FIG. 9 is flowchart of the basic program loop of the software stored in the read-only memory of a cartridge, according to a preferred embodiment of the invention.

Thus, the division of memory addressed by the address lines as asserted on address lines 108 and chip select line 98 determines how lines 102, 104, 106 and 108 are asserted. A memory map of the ECG-monitoring device according to a preferred embodiment is shown in FIG. 8. Still referring to FIG. 7, addressing an address on lines 108 and chip select line 98 within the ROM address space (addresses 0000–6FFF, as shown in FIG. 8), while read line 101 is also asserted to represent a read (note that the read line 101 is directly coupled to the read line of the ROM). causes the data from the ROM to be put on the bus. The ROM address space holds the program, cartridge information, etc. Similarly, addressing an address as asserted on lines 108 and chip select line 98 within the A/D start_conversion range (addresses 7800–7BFF, as shown in FIG. 8), causes the PAL 100 to assert the A/D chip_select line 102. This chip_select line 102 is the same as CHIP_SELECT 88 of FIG. 6, and thus assertion of line 102 begins the conversion process described in conjunction with FIG. 6. (That is, the static ram mode of the A/D is used to start the conversion.)

Addressing an address as asserted on lines 108 and chip select line 98 within the A/D read_conversion range (addresses 7C00–7FFF, as shown in FIG. 8), while concurrently asserting read line 10 1, causes the PAL 100 to assert the A/D chip_select line 102 and the A/D read line 106. Chip_select line 102 is the same as CHIP_SELECT of FIG. 6, and read line 106 is the same as READ 90 of FIG. 6. Therefore, assertion of lines 102 and 106 causes the A/D to put the converted data on the data bus, as has been described in conjunction with FIG. 6. Finally, addressing an address as asserted on lines 108 and chip select line 98 within the multiplexer control range (addresses 7000–77FF, as shown in FIG. 8) causes the PAL 100 to toggle the latch enable line 108. The latch 94 then latches the least significant address values (i.e., on lines 96), which correspond to the multiplexer desired state, as has been described.

Thus, as shown in FIG. 7, performing a read to within the multiplexer range causes PAL 100 to send a latch enable signal to the octal latch 94. The latch 94, in turn, stores the six least significant address lines for controlling the analog multiplexing circuit. Therefore, proper selection of the addresses within the mux address range sets the mux control states. As has been described, the contents of the latch are optically isolated via the isolators, and control the analog multiplexing circuit. The higher address lines A10–A15 of the sixteen-bit address bus of the Gameboy device, as well as the device's read and write control lines, are used to partition the bus space available into regions for the ROM, the A/D converter, and the analog multiplexer circuit.

It is believed that unused circuitry within the PAL can be used to interface digital potentiometer integrated circuits to incorporate multiple gain settings within an embodiment of the invention. Such digital potentiometers would interface with the AD625 instrumentation amplifier, replacing the discrete resistors currently utilized. The gain would then be on-screen programmable from within the ECG-monitoring device itself. It is believed that the addition of this circuitry would impose only slight additional cost.

Referring back to FIG. 4, ROM 78 contains the code executed by the NINTENDO GAMEBOY device to control the sampling and display of ECG waveforms. The invention is not limited to a particular type of ROM. Programmable read-only memories (PROMs), erasable programmable read-only memories (EPROMs), and electrically erasable programmable read-only memories (EEPROMs), are all within the scope of the invention. Preferably a 27C256 EPROM is utilized, as known within the art. The output enable of this EPROM is tied active, and the select and read pins are used to control the ROM operations. The read pin is attached directly to the read line of the NINTENDO GAMEBOY device, and the chip_select pin is controlled by the interface 74 as has been described.

The program utilized in a current preferred embodiment utilizes less than five kilobytes of the 256 kilobytes available in the 27C256 EPROM. The extra storage provides for later contemplated expansion of the preferred embodiment (to include QRS detection routines, for example). As known within the art, however, the Nintendo Gameboy device cannot address more than thirty-two kilobytes of memory without bank switching. Therefore, insofar as more than thirty-two kilobytes of the memory available within the 27C256 EPROM is used, bank switching must be used. Furthermore, it is contemplated that larger ROMs having even more storage capability can easily be utilized to expand the memory capability of the ECG-monitoring device. The program utilized in the current preferred embodiment is described in the following section.

Software Implementation

The software residing with the ROM of the digital section is executed by the processor of the computerized platform. In the preferred embodiment of a NINTENDO GAMEBOY device, the processor is a custom eight-bit Z80 central-processing unit running at 4.19 MHZ. Many of the peripheral functions such as serial communication and sound generation are integrated within this main processor. The CPU also contains an internal ROM.

The software in a preferred embodiment is written in assembly language, using an instruction set very similar to that of a non-custom Z80 microprocessor. The public domain TASM table assembler is used to write the software, and is available from Speech Technology Inc., of Issaquah, Wash. Version 2.9 of the software is specifically used. A list of opcodes specific to the NINTENDO GAMEBOY device, described in "Summary of Gameboy Opcodes," at the Internet world-wide-web URL address "Http://fly.hiwaay.net/-jfrohwei/gameboy/opcodes.html," which is hereby incorporated by reference, is used in conjunction with the TASM assembler. A plug-in table of opcodes specific to the NINTENDO GAMEBOY device, included in a zip file at the Internet world-wide-web URL address "http://fly.hiwaay.net/-jfrohwei/gameboy/tasm69.zip," which is hereby incorporated by reference, is also used in conjunction with the TASM assembler. The "Virtual Gameboy" software emulator, described at the Internet world-wide-web URL address "http://www.freeflight.com/fms/VGB/" is also of utility in programming the NINTENDO GAMEBOY device.

The programming of the NINTENDO GAMEBOY device is known within the art. The description of the device here serves as a summary only to provide a general context for the programming of the software for a diagnostic medical device according to the invention. General information is also available in the Oakada et al. references previously incorporated by reference. The NINTENDO GAMEBOY device for the most part has a large continuous memory block in the ROM. Graphics programming relies on characters and sprites. Both a background and a foreground can be programmed, each with a separate character set. Movement is accomplished by either redrawing the object on the screen (common for foreground objects) or setting scroll registers to scroll the screen (common for backgrounds and maps).

It is believed that the NINTENDO GAMEBOY device has at least one internal security scheme built in, as described in the Oakada et al. references. These schemes are known within the art. The first scheme involves a quick transfer from a ROM cartridge to the NINTENDO GAMEBOY device. The NINTENDO GAMEBOY device runs the program specified in the cartridge only if the information transferred matches that of a previously defined key. The specific process used to program a cartridge ROM in accordance with this security scheme is known within the art and described in the Internet world-wide-web URL address http://fly.hiwaay.net/-jfrohwei/Gameboy/gbspec.txt, which is hereby incorporated by reference.

Two other levels of security are present in the NINTENDO GAMEBOY device. A checksum value is required to be calculated, and is roughly the sum of all the bytes in the program noted at the end of the program. It is believed, however, that although all NINTENDO GAMEBOY device programs have checksums computed and placed at the end, the NINTENDO GAMEBOY device runs programs even if their checksums are incorrect. Finally, a complement check is computed as the sum of the bytes in the header of the program subtracted by one and then two's complemented. The complement check is required by the NINTENDO GAMEBOY device, however, unlike the checksum value. Both the checksum value and the complement check are known within the art, and the specific processes used to program a cartridge ROM in accordance with these security schemes are also known within the art and are described in "Gameboy Authentication Explained," at the Internet world-wide-web URL address http://www.futureone.com/-damaged/Consoles/Gameboy/auth.html, which is hereby incorporated by reference. Other information regarding the security schemes are described in references at the Internet world-wide-web URL addresses http://www.futureone.com/-damaged/Consoles/Gameboy/gbsum.html, http://www.futureone.com/-damaged/Consoles/Gameboy/utils.html, and http://fly.hiwaay.net/ jfrohwei/Gameboy/gbspec.txt, all of which are also hereby incorporated by reference.

Figure 9:
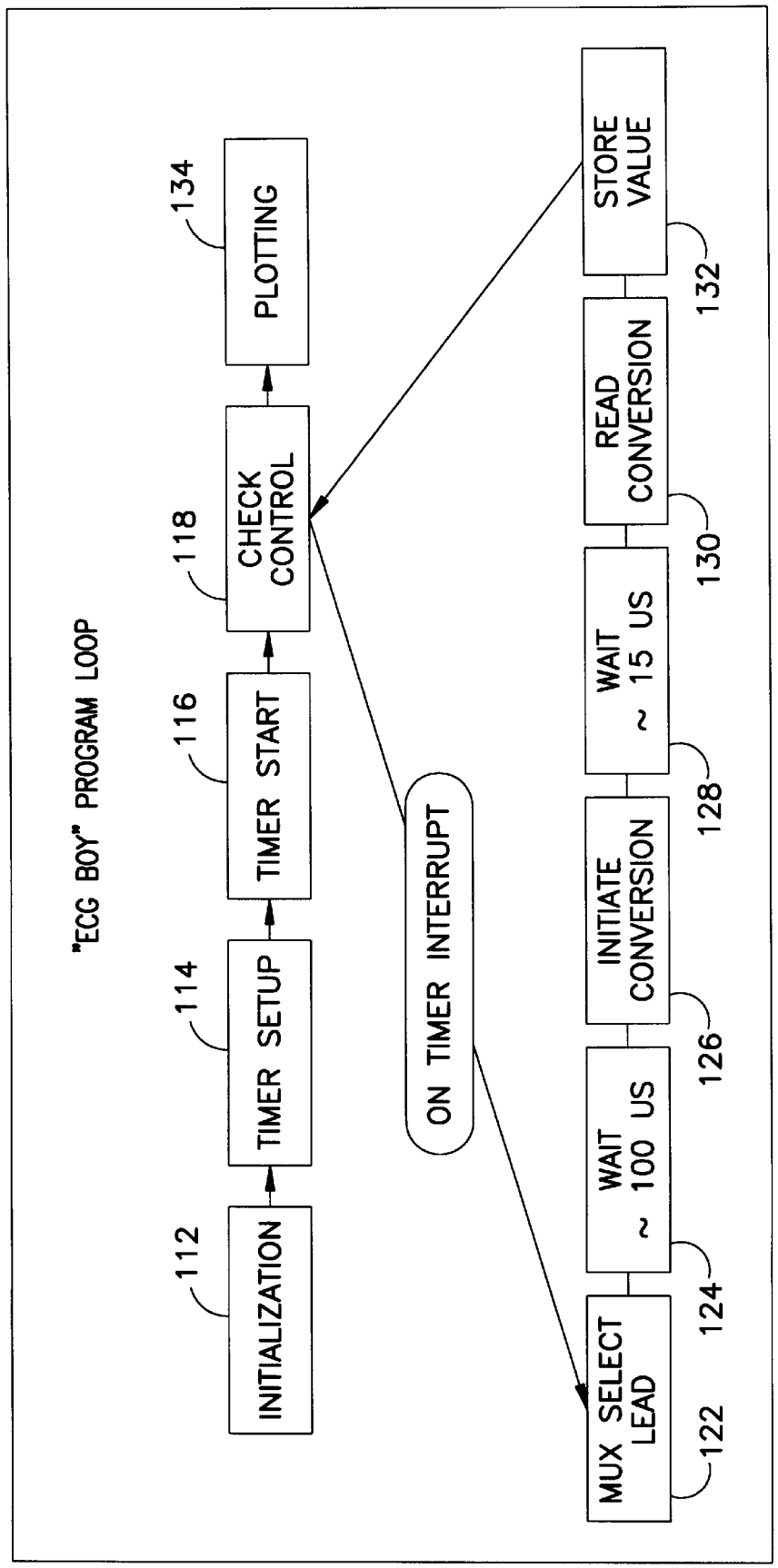

Referring now to FIG. 9, a flowchart of the basic program loop of the software stored in the ROM of the digital section of the cartridge, according to a preferred embodiment of the invention, is shown. In step 112, the NINTENDO GAME platform (a type of cartridge-based portable video game system platform) is initialized (i.e., when the device is first turned on, etc.). The specific sequence is step 112 is power on, followed by a security check as has been described. In step 114, the internal timer (i.e., a timer counting 3.4 milliseconds) is set up, and then started in step 116.

In step 118, the program actually obtains the digitized ECG waveform. This step is accomplished at every condition 120; that is, at every timer interrupt (i.e., every 3.4 milliseconds, as has been described). In other words, step 118 is programmed preferably as an interrupt service routine (ISR). The analog multiplexer control lines corresponding to a desired lead are first selected in step 122. The multiplexer control line values are not changed unless the user selects a different lead or calibration signal. The process is delayed 100 microseconds in step 124 to ensure that the data from the leads have bubbled through the multiplexer and the amplifier section, and are present at the A/D converter inputs.

The program then initiates A/D conversion in step 126 as has already been described, waiting at least 15 microseconds in step 128 to ensure that conversion has been completed by the converter. The converted ECG waveform (i.e., digitized waveform) is read in step 130, stored in step 132, and then plotted on the display of the NINTENDO GAMEBOY device in step 134. A circular buffer is maintained in which the converted ECG waveform is stored for display. The converted points are plotted in a window on the screen from left to right, and then cleared for the next segment.

The rate at which this occurs depends upon a time scale factor selected by the user. This factor lets the user view the signal over longer or shorter periods of time (i.e., zooming in or out if desired). The NINTENDO GAMEBOY device is capable of displaying only 144 pixels across the screen at a time, so the scale factor is required to display longer lengths of time. The scale factor is determined by plotting more than one converted (Y) value for each particular time (X) value. Qualitatively, this has proven more visually representative of the ECG waveforms than only plotting, for example, every other digitized point.

Other Implementation Issues

As has been described, the overall ECG-monitoring device according to a preferred embodiment is divided into isolated and non-isolated sections. All parts of the circuit that come into contact with the host body are optically isolated from the NINTENDO GAMEBOY device, and the non-isolated section of the circuit. Separate power supplies for each section are necessary to achieve this. The isolated section requires ±6 volt supplies, while the non-isolated section requires ±6 and ±5 volt supplies. In one embodiment, two nine-volt batteries and two regulator integrated circuits (e.g., 7806, 7906 devices) comprise the isolated supplies, and two nine-volt batteries and three regulator integrated circuits (e.g., 7805, 7806, 7906 devices) comprise the non-isolated supplies. The NINTENDO GAME platform (a type of cartridge-based portable video game system platform) device itself uses four AA batteries.

It is contemplated that further refinement of the design disclosed herein may result in reduction of the power consumption and the size of the requisite battery pack. For example, if charge-pump inversion integrated circuits are added, the number of nine-volt batteries and regulators necessary may be reduced by one-half. Such integrated circuit inversion devices convert a positive into a negative potential or vice-versa at a very high efficiency, at the low currents involved. One nine-volt battery could be regulated to the required positive six-volt level, then inverted to negative six volts. This eliminates one battery and one regulator with the added expense of the inversion device. This alternative design may also be accomplished on the non-isolated section.

A further contemplated alternative embodiment that reduces power consumption is the utilization of surface-mount components directly on a printed circuit board of the cartridge, instead of discrete components. As a general rule, surface-mount components require less power than do discrete components. If power usage is sufficiently reduced, the NINTENDO GAMEBOY device itself may be able to supply sufficient power to at least the non-isolated section of the circuit.

The parts used in building the ECG-monitoring device are all commonly available, from such sources as Digi-key Corp., of Thief River Falls, Minn., and Newark Electronics, of Troy, Mich. The AD 625 instrumentation amplifier in particular is manufactured and directly available from Analog Devices, of Norwood, Mass. Like all the other components, however, the invention is not particularly limited to any delineated component herein.

The ECG-monitoring device according to the preferred embodiment as has been described is believed to be inexpensively manufactured. Much of the savings associated with the device is based on the fact that a mass-produced platform, the NINTENDO GAMEBOY device, containing many of what are usually expensive components (screen, CPU, RAM, etc.), is utilized. As has been described, it is believed that the NINTENDO GAMEBOY device costs approximately fifty dollars. The component cost of the cartridge device described herein at the time of the filing of this application is approximately $125, and in quantities of 100 or more it is believed should decrease to $75 or less, bringing the total system cost with NINTENDO GAMEBOY device to $125. This is the component cost, and does not include manufacturing, packaging, or other costs. Further refinement of the design may also reduce costs.

Conclusion

A portable modular diagnostic medical device has been described. The device is portable in that it is based on a portable handheld multipurpose computerized platform. The device is modular in that different cartridges having different diagnostic medical functionality can be plugged into the device. Clinicians are able to take this portable instrumentation device to remote locations easily. The device is simple to operate. In the preferred embodiment described, ECG waveforms are displayed on the screen on-line in real time. This provides immediate and direct access to data without requiring transmission to other support hardware. The device is relatively inexpensive as well.

Although specific embodiments have been illustrated and described herein, it will be appreciated by those of ordinary skill within the art that any arrangement which is calculated to achieve the same purpose may be substituted for the specific embodiments shown. This application is intended to cover any adaptations or variations of the present invention. For example, the invention has been shown in relation to a NINTENDO GAMEBOY device. However, any portable handheld multipurpose computerized platform conforming to the claimed invention is amenable, such as a personal digital assistant (PDA). For further example, the invention has been shown in relation to an ECG device. However, any predetermined diagnostic medical function is amenable to the invention. Therefore, it is manifestly intended that this invention be limited only by the claims and equivalents thereof.

I claim:

1. A portable and modular electrocardiogram (ECG) medical device comprising:
    a preprogrammed cartridge comprising:
        a housing;
        a connector partially disposed within the housing;
        a plurality of leads, each lead detecting a lead signal;
        an analog circuit to measure an ECG from the plurality of leads;

a digital circuit for digitizing the ECG into ECG data and to send the ECG data through the connector regarding the ECG means for storing predetermined ECG function software; and, a portable hand-held multipurpose computerized base unit comprising:

a second housing;

a slot disposed within the second housing such that the connector of the preprogrammed cartridge is removably insertable within the slot;

a display screen disposed within the second housing and for displaying the ECG data as a waveform according to a predetermined scale factor;

a select control disposed within the second housing to toggle a lead signal displayed on the display screen, the lead signal comprising the lead signal of one of the plurality of leads of the preprogrammed cartridge;

a joy pad disposed within the second housing and having left, right, up and down arrow keys, the left and the right arrow keys to change the scale factor of the ECG waveform as displayed on the display screen;

an option menu displayed on the display screen in conjunction with the waveform of the ECG and having a plurality of options regarding the ECG and selectable via the up and the down arrow keys of the joy pad, the plurality of options including:

a calibration control option to calibrate an amplitude of the waveform of the ECG against a predetermined reference voltage; and a second digital circuit within the second housing for receiving the ECG function software and for programming and controlling the base unit, display screen, select control, joypad, and option menu according to the software.

2. The medical device of claim 1, wherein the scale factor is such that a plurality of data points of the waveform of the ECG is displayed on the display screen such that for each of a plurality of X values of the display screen, more than one of the plurality of data points of the waveform of the ECG is plotted as corresponding Y values of a plurality of Y values of the display screen.

3. The medical device of claim 1, wherein the plurality of options of the option menu further comprises:

a grid control option to toggle a displayed grid on the display screen on and off; and, a select lead control option to toggle a displayed lead signal displayed on the display screen.

4. The medical device of claim 3, wherein the plurality of options of the option menu further comprises:

a detect control option to begin display of the waveform of the ECG measured by the analog circuit on the display screen; and, a stop control option to stop the display of the waveform of the ECG measured by the analog circuit on the display screen.

* * * * *